United States Patent [19]
Lee

[11] Patent Number: 5,384,404
[45] Date of Patent: Jan. 24, 1995

[54] PROCESS FOR MANUFACTURING MELAMINE FROM UREA

[76] Inventor: Jing M. Lee, 11602 Blair Meadow, Stafford, Tex. 77477

[21] Appl. No.: 147,848

[22] Filed: Nov. 5, 1993

[51] Int. Cl.⁶ .................................... C07D 251/60
[52] U.S. Cl. ................................ 544/201; 202/81
[58] Field of Search ............... 544/201; 564/32; 202/81

[56] References Cited

U.S. PATENT DOCUMENTS

| | | | |
|---|---|---|---|
| 2,549,492 | 4/1951 | Wilmington | 544/201 |
| 3,132,143 | 5/1964 | Fogagnolo et al. | 544/201 |
| 3,251,843 | 5/1966 | Murata et al. | 544/201 |
| 3,492,302 | 1/1970 | Abe et al. | 544/201 |
| 3,598,818 | 8/1971 | Krekels | 544/201 |
| 3,682,911 | 8/1972 | Kaasenbrood et al. | 544/201 |
| 4,156,080 | 5/1979 | van Hardeveld | 544/201 |
| 4,565,867 | 1/1986 | Thomas et al. | 544/201 |

Primary Examiner—John M. Ford
Assistant Examiner—Y. N. Gupta
Attorney, Agent, or Firm—Daniel N. Lundeen; Andrew S. Pryzant

[57] ABSTRACT

An improved process for manufacturing melamine from urea simplifies the recovery of melamine, carbamate and ammonia from a fluidized bed reactor effluent stream by operating the process at a pressure between 1.4 and 2 MPa. In such a manner, a carbamate solution can be produced at a sufficiently high concentration for use in a urea plant without an intervening concentration step. In addition, ammonia recycled as a fluidizing gas can be condensed against cooling water to permit easy separation of noncondensables such as oxygen which used in the process as a passivator for carbamate corrosion inhibition. The melamine product is produced as an aqueous solution free of melamine solids. Heat is recovered from the carbamate condensation and used for the vaporization of ammonia which is recycled to the reactor for fluidization.

11 Claims, 1 Drawing Sheet

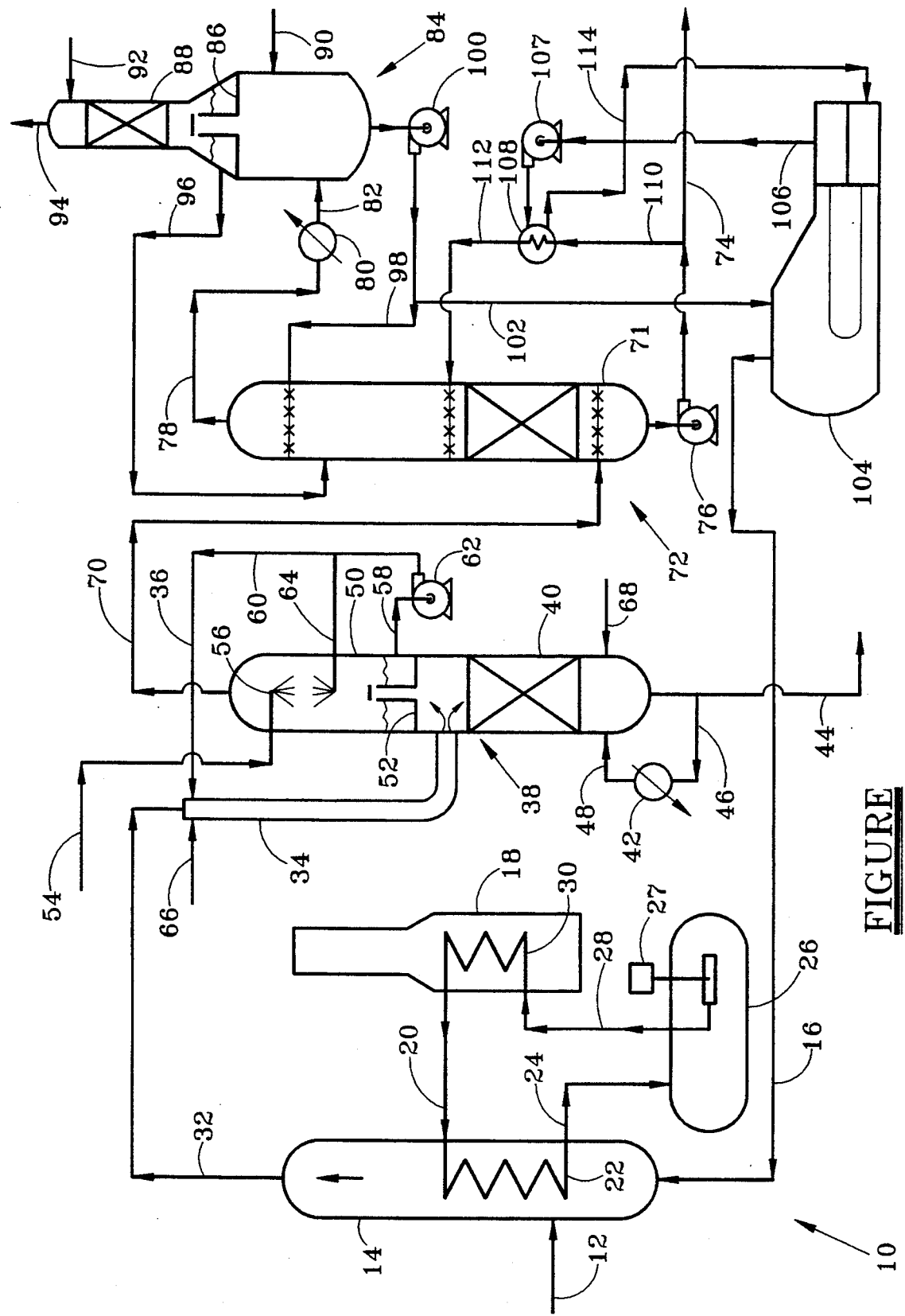
FIGURE

PROCESS FOR MANUFACTURING MELAMINE FROM UREA

FIELD OF THE INVENTION

The present invention relates to an improved process for manufacturing melamine from urea.

BACKGROUND OF THE INVENTION

Melamine is generally produced by heating molten urea in an ammonia-fluidized catalytic reactor above 350° C. Known as the Stamicarbon process, the fluidized catalytic preparation of melamine from urea is described in U. S. Pat. Nos. 3,598,818 to Krekels and 3,682,911 to Kaasenbrood et al. Typically, the melamine in the reaction effluent is quenched with an aqueous liquid to extract the melamine. Carbon dioxide and water vapor remaining in the reaction effluent are absorbed by an ammonia absorbent to produce an aqueous ammonium carbamate solution useful as a reactant for urea production. Excess ammonia from the absorption step is recycled to the melamine reactor as a catalyst fluidizing gas and to suppress by-product reactions. Currently, fluidized bed melamine reactors are operated at a relatively lower pressure (less than about 1.0 MPa) to permit ammonia recovered from the reaction effluent gas to be recycled directly to the melamine reactor.

Several drawbacks to the prior art are evident. The use of lower pressure in the melamine reactor produces an effluent stream having a relatively high water partial pressure following melamine recovery. Upon $CO_2$ absorption (and carbamate condensation), the carbamate solution produced is generally too dilute for recycling to the urea plant without an intervening concentration step. Further, the pressure in the ammonia recovery is too low to permit economical ammonia condensation without expensive refrigeration. Thus, the use of oxygen passivation for inhibiting corrosion in the quenching and stripping equipment is limited since there is no provision for separating the oxygen from the ammonia recycled to the reactor. In addition, melamine recovery in the Stamicarbon process produces a slurry containing melamine solids. The presence of solids can lead to plugging problems and require the use of solids separation equipment such as cyclones.

SUMMARY OF THE INVENTION

A process for manufacturing melamine from urea is enhanced by incorporation of several improvements. Improvements include increasing the system pressure to a range of from about 1.4 to 2 MPa. Thus, the partial pressure of water vapor in a $CO_2$ absorption tower is lowered to increase the concentration of ammonium carbamate solution produced for recycle to urea production. A higher system pressure also enables an oxygen or air passivating gas to be conveniently used to inhibit carbamate corrosion because passivating gas can be subsequently separated as a noncondensable stream following an ammonia condensation step wherein cooling water is conveniently employed. Ammonia condensate can then be vaporized for recycle to the reactor as a catalyst fluidizing gas using heat supplied by carbamate condensation. Melamine product is recovered as an unsaturated aqueous solution following quench and wash steps using a sufficient volume of aqueous mother liquor from a melamine purification unit to eliminate formation of melamine solids and obviate solids separation equipment.

In one embodiment, the present invention provides a process for manufacturing melamine from urea. The process includes the following steps: (a) urea and a fluidizing amount of ammonia are supplied to a reactor at a pressure from about 1.4 MPa to about 2.0 MPa and a temperature effective to substantially convert the urea in the presence of a catalyst to melamine and form an effluent stream comprising melamine, ammonia and carbon dioxide; (b) the effluent stream is quenched to form a vapor-liquid mixture essentially free of solids; (c) the vapor-liquid mixture is separated into a concentrated aqueous melamine product stream essentially free of solids, ammonia and carbon dioxide, and a high pressure vapor stream essentially free of urea and melamine; (d) the high pressure vapor stream is contacted, preferably in a single stage with an aqueous ammonia stream in an absorption zone refluxed with liquid ammonia to form a concentrated aqueous ammonium carbamate stream and an overhead ammonia vapor stream essentially free of carbon dioxide; (e) ammonia is condensed from the overhead vapor stream to form a liquid ammonia stream; and (f) a portion of the liquid ammonia stream is vaporized to form the fluidizing ammonia for supply to the reactor. The absorption zone is preferably cooled to recover heat for the ammonia vaporization step.

In a preferred embodiment, a relatively cold heat transfer fluid medium is circulated in heat exchange with the absorption zone to form a relatively hot fluid medium, and the hot fluid medium is circulated in heat exchange with the vaporizing ammonia to form the cold fluid medium. A passivation gas is preferably introduced to the quenching or stripping step wherein the passivation gas includes oxygen or air. The passivation gas is preferably removed in an overhead stream of noncondensables from the ammonia condensation step. The noncondensables stream is preferably contacted with water to remove ammonia therefrom, and form a noncondensables stream essentially free of ammonia and the aqueous ammonia stream for the contacting step (d). Preferably, the reactor temperature is from about 380° to about 430° C. and the reactor pressure is from about 1.5 to about 1.8 MPa. The concentrated aqueous ammonium carbamate stream preferably comprises from about 65 to about 80 percent carbamate by weight. The separation step (c) preferably includes stripping the melamine solution to reduce the carbon dioxide and ammonia content in the melamine product stream to less than 0.5 percent by weight.

In another embodiment, the present invention provides apparatus for manufacturing melamine from urea. A reactor is provided for converting urea and a fluidizing amount of ammonia in the presence of a catalyst at a pressure from about 1.4 MPa to about 2 MPa and an effective temperature into melamine and forming a reactor effluent stream comprising melamine, ammonia, carbon dioxide and water. A quench zone is provided for mixing the effluent stream with an aqueous quench stream to form a vapor-liquid mixture essentially free of solids. A separation zone is provided for separating the vapor-liquid mixture into a concentrated aqueous melamine product stream essentially free of solids, ammonia and carbon dioxide, and a high pressure vapor stream essentially free of urea and melamine. An absorption zone is provided for contacting the high pressure vapor stream with aqueous ammonia and refluxing the high pressure vapor stream with liquid ammonia to form a concentrated aqueous ammonium carbamate stream and an overhead ammonia vapor stream essentially free of carbon dioxide and water vapor. A condenser is provided for condensing the overhead ammonia vapor from the absorption zone to form a liquid ammonia stream. A heat exchanger is provided for vaporizing the liquid ammonia stream to form a fluidizing ammonia stream. A line is provided for supplying the fluidizing ammonia stream to the reactor.

In a preferred embodiment, a heat transfer medium is provided for circulating in heat exchange with the absorption zone to form a relatively hot fluid medium for circulation in heat exchange with the vaporizing ammonia to form the cold fluid medium. A passivation gas including oxygen or air is preferably introduced to the quench or separation zones to inhibit corrosion. The passivation gas is preferably removed in an overhead stream of noncondensables from the ammonia condenser. A noncondensables wash zone is preferably provided to remove ammonia therefrom, and form a noncondensables stream essentially free of ammonia and the aqueous ammonia stream for the absorption zone. Preferably, the reactor is operable at a temperature from about 380° to about 430° C. and a pressure from about 1.5 to about 1.8 MPa. The concentrated aqueous ammonium carbamate stream preferably comprises from about 65 to about 80 percent carbamate by weight. The melamine separation zone is preferably operable to strip the melamine with steam to reduce the carbon dioxide and ammonia content in the melamine product stream to less than 0.5 percent by weight.

BRIEF DESCRIPTION OF THE DRAWING

The FIGURE is a schematic flow diagram of the melamine synthesis process of the present invention.

DETAILED DESCRIPTION OF THE INVENTION

An improved process for synthesizing melamine from urea simplifies, in part, the recovery of melamine, carbamate and ammonia from a fluidized bed reactor effluent by increasing the pressure of the system. Operating at a higher pressure reduces the partial pressure of water in a carbamate recovery stream and produces a carbamate solution suitable for recycle to urea production without an intervening concentration step. In addition, cooling water can be used to condense ammonia for separation of noncondensables such as an oxygen passivating gas. The condensed ammonia stream can be vaporized for recycle to the reactor as a catalyst fluidizing gas by the heat of carbamate condensation. The melamine product can be formed as an aqueous solution free of solids for easier handling.

Referring to the FIGURE, a melted urea stream 12 above 140° C. is directed to a melamine reactor 14 in an improved melamine manufacturing process 10 according to the present invention. As is well known in the art, urea is converted into melamine, carbon dioxide and ammonia in the presence of a bed of fluidized catalyst such as alumina silicate at an elevated temperature and pressure. The molten urea stream 12 is typically sprayed into the catalyst bed fluidized by a sufficient flow of gaseous ammonia fed to the bottom of the reactor 14 through line 16. The catalyst fluidization gas also assists in the suppression of melamine by-product reactions.

In the practice of the present invention, the reactor 14 preferably operates at a temperature of from about 380° C. to about 430° C. and a pressure sufficiently high to substantially convert urea into melamine and recover an ammonium carbamate solution having a suitably high carbamate concentration for recycle to a urea plant (not shown) without intervening carbamate concentrating steps. (Ammonium carbamate being the well known product of $CO_2$ absorption by an aqueous ammonia sorbent.) Typically, reactor 14 has an operating pressure of from about 1.4 MPa to about 2.0 MPa, preferably from about 1.5 MPa to about 1.8 MPa.

Reaction heat for the reactor 14 can be supplied by any acceptable external, indirect heating source employing a suitable high temperature heat transfer fluid stable at reaction conditions. A molten metal or inorganic salt which is non-corrosive to the heat transfer equipment is conveniently employed. The present molten salt heat source includes an closed loop system wherein a molten salt heating fluid is circulated between a heater 18 such as a fired furnace and the reactor 14. A hot molten salt stream is fed through line 20 from the heater 18 to heat exchange tubes 22 in the reactor 14 wherein heat is exchanged with the fluidized catalyst bed to maintain the catalyst bed at the desired reaction temperature. A cooled molten salt stream is withdrawn from the reactor tubes 22 through line 24 for return to the heater 18 via a reservoir tank 26. Molten salt from the tank 26 is withdrawn by pump 27 and circulated through line 28 to heat exchange tubes 30 of the furnace 14 wherein the molten salt becomes reheated.

Following conversion in the reactor 14, a reaction effluent vapor stream containing melamine, ammonia, carbon dioxide and essentially free of urea is removed through line 32 for melamine and $CO_2$ removal. A purified ammonia stream is then recycled to the reactor as the catalyst fluidizing gas as mentioned above. The hot effluent vapor 32 is first quenched in a quench pipe 34 by contact with a quench stream comprising a sufficient quantity of an aqueous-based mother liquid from a melamine purification unit (not shown) fed through line 36 to form a vapor-liquid mixture. In the quench pipe 34, melamine in the reactor effluent vapor 32 becomes dissolved in the quench mother liquid. The vapor-liquid mixture cooled to a temperature on the order of 140° C. is then phase separated to produce a liquid melamine-rich product stream. The melamine-rich solution is preferably separated from the vapor phase in a combined quench/stripping tower 38 receiving the vapor-liquid mixture at a feed zone above a stripping zone 40.

The melamine-rich solution flows downward through the stripping zone 40 wherein dissolved ammonia and $CO_2$ are essentially stripped therefrom by steam generated by a reboiler 42. A melamine product stream at a temperature on the order of 200° C. is removed from the stripping zone 40 for feed through line 44 to the melamine purification unit (not shown). The melamine product stream 44 should have less than about 0.5 weight percent dissolved ammonia and carbon dioxide gas, more preferably less than 0.1 percent by weight of dissolved gas. The concentration of melamine in the product stream 44 is less than the melamine saturation point to prevent precipitation of melamine solids. A portion of the melamine solution is removed from the product stream 44 through line 46 to the reboiler 42 where it is heated and returned to the stripping zone 40 through line 48. The reboiler 42 is preferably heated using high pressure stream.

Vapor components (primarily ammonia, carbon dioxide, water and residual melamine) from the mixed vapor-liquid stream, and stripped vapor from the stripping zone 40 flow upward into an upper wash zone 50 of the tower 38. The lower and upper zones 40, 50 are separated by an appropriately designed withdrawal tray 52. In the wash zone 50, the vapor is scrubbed of residual melamine by the mother liquid stream (from melamine purification) introduced through line 54. Mother liquid can be introduced by means suitable for enhancing liquid-gas contact (e.g. through a spray nozzle 56). Following liquid-gas contacting, mother liquid accumulating in the tray 52 is withdrawn though line 58 and pumped through line 60 via pump 62 as the quench stream for contact with the hot reaction effluent stream 32 in the quench pipe 34. A portion of the mother liquid stream in line 60 is preferably sprayed into the wash zone 50 through line 64 as an additional wash stream.

In a preferred embodiment, a small amount of passivation gas comprising oxygen or air is preferably introduced through line 66 at the quench pipe inlet and through line 68 at the bottom of the stripping zone 40 for corrosion protection of the entire carbamate system (i.e. those portions of the process wherein ammonium carbamate is produced). It is understood that while the above detailed points for passivation gas injection are preferred, additional and/or alternative locations for passivation gas introduction could also be used.

An essentially melamine-free vapor stream comprising ammonia, carbon dioxide, water vapor and passivation gas is withdrawn from the wash zone 50 through line 70 for feed below an absorption zone 71 of a carbamate absorber 72. In the carbamate absorber 72, the melamine-free vapor is contacted with an absorbent, preferably comprising liquid ammonia and aqueous ammonia, to absorb carbon dioxide and water and produce a concentrated ammonium carbamate condensate stream. The absorber 72 generally includes vapor-liquid contacting elements and nozzles to enhance the absorption process. A spent absorbent solution comprising primarily condensed ammonium carbamate is removed from the absorber bottom through line 74 for feed via pump 76 to a urea production unit (not shown). The spent absorbent solution, preferably after a single-stage condensation, comprises from about 65 to about 80 percent by weight ammonium carbamate, and more preferably above 70 percent by weight ammonium carbamate, so that no additional process steps are necessary (prior to use in the urea plant) to enhance the concentration of the carbamate solution from the line 74.

Following absorption of the carbon dioxide and water, an ammonia-rich vapor stream which is essentially $CO_2$-free and water-free is removed overhead through line 78. The ammonia-rich stream 78 is preferably condensed by water cooled condenser 80 to form a vapor-liquid stream containing liquid ammonia and noncondensable gas. The vapor-liquid ammonia stream is fed through line 82 to the bottom of a vapor-liquid separator 84 wherein liquid ammonia is separated from the noncondensable gas. The noncondensable stream passes upward through a withdrawal tray 86 to a water wash zone 88. A liquid ammonia makeup stream is introduced as needed through line 90. Ammonia in the noncondensable stream is washed therefrom by contact with water condensate introduced to the wash zone 88 through line 92. An essentially ammonia-free noncondensable stream is vented from the wash zone 88 through line 94. An aqueous ammonia stream accumulating on the tray 86 is preferably drawn off through line 96 as a liquid absorbent for $CO_2$ absorption in the carbamate absorber 72 as mentioned previously.

One portion of the ammonia condensate accumulating at the bottom of the ammonia separator 84 is pumped via pump 100 through line 98 as a liquid ammonia reflux to the carbamate absorber 72 above the aqueous ammonia feed. A second portion thereof is taken off through line 102 to ammonia vaporizer 104 for recycle via line 16 to the reactor 14 for catalyst fluidization as previously mentioned. Ammonia vaporization is conveniently effected by a closed-loop circulating pump using heat generated by carbamate condensation in the absorber 72. The ammonia stream 102 is fed shell side to a high pressure vaporization heat exchanger 104. Ammonia is vaporized by an exchange of heat against a hot heat exchange liquid such as water on the tube side and the heat exchange liquid is cooled. The ammonia vapor for catalyst fluidization is directed to the reactor 14 through line 16 as mentioned previously. The cooled heat exchange liquid is withdrawn through line 106 and circulated via a pump 107 to a heat exchanger 108 receiving a side stream 110 of the hot carbamate solution 74. The cooled heat exchanger liquid is reheated in the exchanger 108 by an exchange of heat against the hot carbamate stream 110. A cooled carbamate stream is returned to the absorber 72 via line 112. The reheated heat exchange fluid is circulated back to the ammonia vaporization exchanger 104 through line 114. As is well understood, the amount of the carbamate circulated through the line 110 will depend on the heat balance or cooling required for the carbamate absorber 72.

The present invention can be further illustrated by reference to the following example.

EXAMPLE

The simplified melamine process of the present invention as shown in the FIGURE is evaluated by standard process design techniques to estimate the condition of selected process streams and vessels. The evaluation assumes a melamine formation rate of 30–34 weight percent of the incoming urea (the remainder being converted to ammonia and $CO_2$). The carbamate stream 74 from the carbamate absorber 72 comprises 75 weight percent ammonium carbamate and 25 weight percent water. Results are presented in the Table.

TABLE

| Process Stream/Equipment | Temp. (°C.) | Press. (MPa) |
| --- | --- | --- |
| Molten salt heater (line 20) | 440 | 0.4 |
| Molten salt tank 26 | 400 | 0 |
| Molten salt pump (line 28) | 400 | 0.4 |
| Reactor (line 32) | 410 | 1.7 |
| Quench pipe 34 | 140 | 1.68 |
| Stripping zone (line 44) | 203 | 1.65 |
| Reboiler 42 | >210 | — |
| Wash zone 50 | 140 | 1.64 |
| Wash pump (line 60) | 140 | 1.9 |
| Absorber, overheads (line 78) | 40 | 1.62 |
| Absorption zone 71 | 100 | 1.64 |
| Carbamate pump (line 74) | 100 | 1.75 |
| Carbamate cooler (line 112) | 80 | 1.75 |
| Ammonia condenser (line 82) | 40 | 1.62 |
| Ammonia separator 84 | 40 | 1.61 |
| Ammonia pump (line 98) | 40 | 1.9 |
| Ammonia vaporizer | 48 | 1.9 |

| Process Stream/Equipment | Temp. (°C.) | Press. (MPa) |
|---|---|---|
| (line 16) | | |

The present melamine synthesis process and apparatus are illustrated by way of the foregoing description and examples. The foregoing description is intended as a non-limiting illustration, since many variations will become apparent to those skilled in the art in view thereof. It is intended that all such variations within the scope and spirit of the appended claims be embraced thereby.

I claim:

1. A process for manufacturing melamine from urea, comprising the steps of:
   (a) supplying urea and a fluidizing amount of ammonia to a reactor at a pressure from about 1.4 MPa to about 2.0 MPa and a temperature effective to substantially convert the urea in the presence of a catalyst to melamine and form an effluent stream comprising melamine, ammonia and carbon dioxide;
   (b) quenching the effluent stream to form a vapor-liquid mixture essentially free of solids;
   (c) separating the vapor-liquid mixture into a concentrated aqueous melamine product stream essentially free of solids, ammonia and carbon dioxide, and a high pressure vapor stream essentially free of urea and melamine;
   (d) contacting the high pressure vapor stream with an aqueous ammonia stream in an absorption zone refluxed with liquid ammonia to form a concentrated aqueous ammonium carbamate stream and an overhead ammonia vapor stream essentially free of carbon dioxide;
   (e) condensing ammonia from the overhead vapor stream to form a liquid ammonia stream;
   (f) vaporizing a portion of the liquid ammonia stream to form the fluidizing ammonia for supply to the reactor.

2. The process of claim 1, comprising cooling the absorption zone in step (d) to recover heat for the ammonia vaporization step.

3. The process of claim 2, comprising circulating a relatively cold heat transfer fluid medium in heat exchange with the absorption zone to form a relatively hot fluid medium, and circulating the hot fluid medium in heat exchange with said vaporizing ammonia to form the cold fluid medium.

4. The process of claim 1, comprising introducing a passivation gas to the quenching or stripping step.

5. The process of claim 4, wherein the passivation gas includes oxygen or air.

6. The process of claim 4, comprising removing the passivation gas in an overhead stream of noncondensables from the ammonia condensation step.

7. The process of claim 6, further comprising contacting the noncondensables stream with water to remove ammonia therefrom, and form a noncondensables stream essentially free of ammonia and the aqueous ammonia stream for the contacting step (d).

8. The process of claim 1, wherein the reactor temperature is from about 380° C. to about 430° C. and the reactor pressure is from about 1.5 to about 1.8 MPa.

9. The process of claim 1, wherein step (d) comprises a single stage condensation and the concentrated aqueous ammonium carbamate stream comprises from about 65 to about 80 percent carbamate by weight.

10. The process of claim 1, wherein the separation step (c) includes stripping the melamine with steam to reduce the carbon dioxide and ammonia content in the melamine product stream to less than 0.5 percent by weight.

11. The process of claim 1, wherein said quenching step (b) is effected in a quench zone wherein the effluent stream is mixed with an aqueous quench stream; said separation step (c) is effected in a separation zone; said condensation step (e) is effected in a condenser; said vaporization step (f) is effected in a first heat exchanger; and the fluidizing ammonia is supplied by a line from the heat exchanger to the reactor.

* * * * *